(12) United States Patent
Casiraro et al.

(10) Patent No.: US 11,918,247 B2
(45) Date of Patent: Mar. 5, 2024

(54) CATHETER FOR ACTIVE SLICING/SCORING AND RELATED METHODS

(71) Applicant: C.R. Bard, Inc., Tempe, AZ (US)

(72) Inventors: Matt Casiraro, Tempe, AZ (US); Katherine Huffer, Chandler, AZ (US); Chad Van Liere, Phoenix, AZ (US)

(73) Assignee: C.R. Bard, Inc., Franklin Lakes, NJ (US)

( * ) Notice: Subject to any disclaimer, the term of this patent is extended or adjusted under 35 U.S.C. 154(b) by 466 days.

(21) Appl. No.: 17/047,494

(22) PCT Filed: Apr. 19, 2018

(86) PCT No.: PCT/US2018/028311
§ 371 (c)(1),
(2) Date: Oct. 14, 2020

(87) PCT Pub. No.: WO2019/203831
PCT Pub. Date: Oct. 24, 2019

(65) Prior Publication Data
US 2021/0113236 A1    Apr. 22, 2021

(51) Int. Cl.
*A61B 17/3207* (2006.01)
*A61B 17/32* (2006.01)

(52) U.S. Cl.
CPC ........... *A61B 17/320783* (2013.01); *A61B 2017/320052* (2013.01); *A61B 2017/320741* (2013.01); *A61B 2017/320791* (2013.01)

(58) Field of Classification Search
CPC ........ A61B 17/3207; A61B 17/320725; A61B 2017/00783; A61B 2017/320741; A61B 2017/320791; A61B 17/32075; A61B 2017/32044
See application file for complete search history.

(56) References Cited

U.S. PATENT DOCUMENTS

| | | | |
|---|---|---|---|
| 5,224,949 A | 7/1993 | Gomringer et al. | |
| 5,256,147 A * | 10/1993 | Vidal | ................. A61B 17/3417 604/274 |
| 5,792,158 A | 8/1998 | Lary | |
| 6,258,108 B1 | 7/2001 | Lary | |

(Continued)

FOREIGN PATENT DOCUMENTS

| | | |
|---|---|---|
| CN | 107753092 A | 3/2018 |
| JP | H0522015 A | 1/1993 |

(Continued)

*Primary Examiner* — Sarah A Long
*Assistant Examiner* — Lindsey Bachman
(74) *Attorney, Agent, or Firm* — Dickinson Wright PLLC; Andrew D. Dorisio

(57) ABSTRACT

A catheter for actively scoring or slicing a lesion. A catheter body includes first and second lateral openings. A selectively deployable cutter is connected to the catheter body. The cutter has a retracted configuration in which it does not perform a slicing or scoring function, such as while tracking through the vasculature, and a deployed configuration for slicing or scoring an obstruction. The cutter may include a plurality of retractable blades, such that when deployed, each blade projects in a different direction, such as from one of the lateral openings. Related methods are also disclosed.

4 Claims, 16 Drawing Sheets

(56) References Cited

U.S. PATENT DOCUMENTS

| | | | |
|---|---|---|---|
| 2003/0139757 A1* | 7/2003 | Lang | A61B 18/1445 606/174 |
| 2004/0122457 A1 | 6/2004 | Weber | |
| 2005/0216019 A1 | 9/2005 | Eckman | |
| 2007/0191875 A1* | 8/2007 | Rehil | A61B 17/3415 606/185 |
| 2009/0254092 A1 | 10/2009 | Albiol Llorach | |
| 2010/0094320 A1 | 4/2010 | Arat et al. | |
| 2010/0268175 A1* | 10/2010 | Lunsford | A61B 17/0218 604/272 |
| 2012/0241188 A1* | 9/2012 | Power | A61B 1/00154 242/615.3 |
| 2015/0238666 A1 | 8/2015 | Clark, III et al. | |

FOREIGN PATENT DOCUMENTS

| | | |
|---|---|---|
| JP | H1094543 A | 4/1998 |
| JP | 2008543421 A | 12/2008 |
| JP | 2012524618 A | 10/2012 |
| JP | 2013526969 A | 6/2013 |
| JP | 2017192815 A | 10/2013 |
| JP | 2014061411 A | 4/2014 |

* cited by examiner

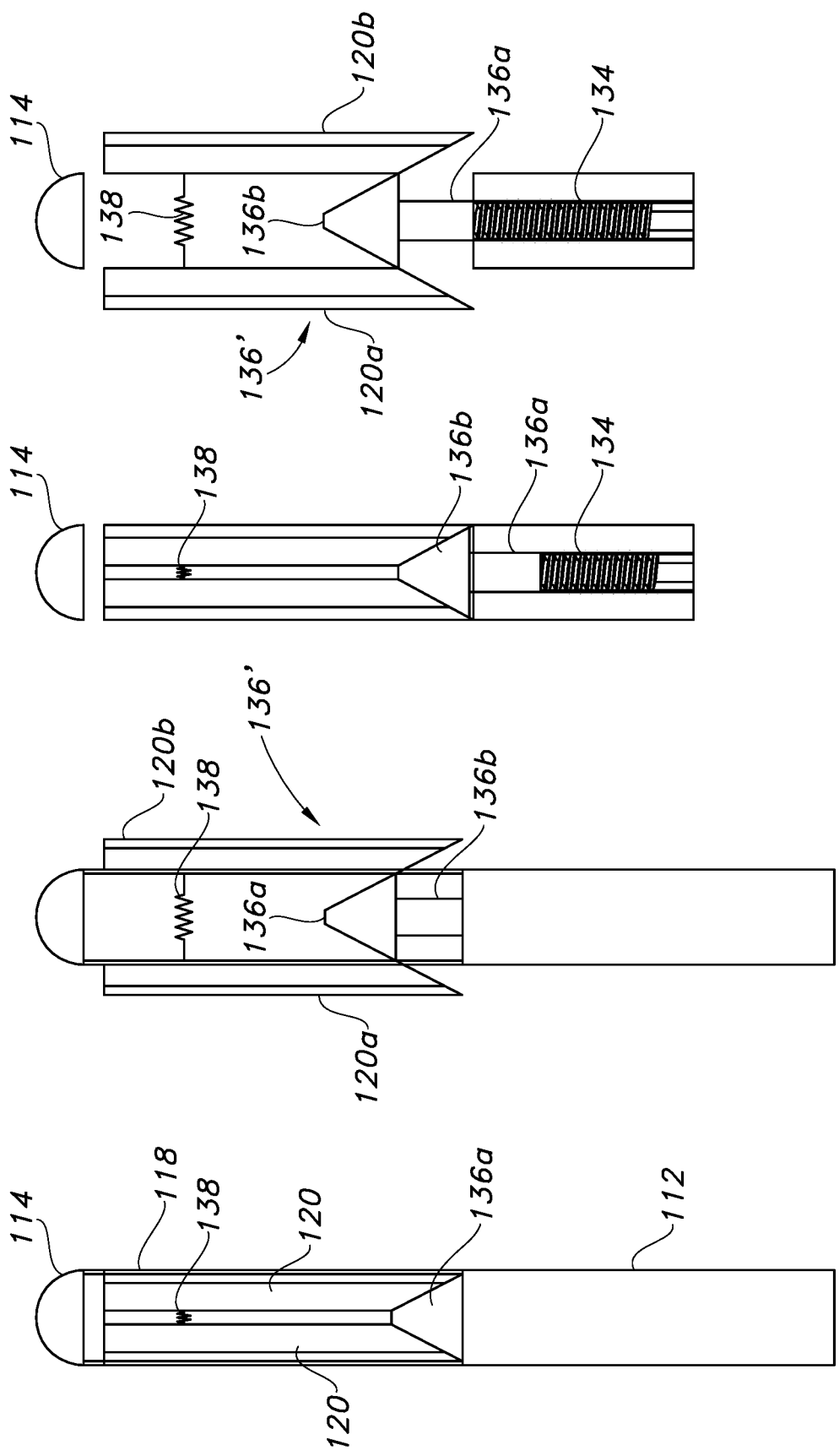

CATHETER FOR ACTIVE SLICING/SCORING AND RELATED METHODS

TECHNICAL FIELD

This disclosure pertains to devices for providing endovascular treatment and, in particular, a catheter with one or more retractable cutters for actively slicing or scoring a lesion or other obstruction in the vasculature.

BACKGROUND

Balloon dilatation catheters are used to treat lesions in the vasculature, such as by way of angioplasty. While successful for use in a variety of applications or locations in the vasculature, some situations call for a different approach in view of the possibility of "elastic recoil," which refers to the inherent resistance of a tissue to changes in shape, and the tendency of the tissue to revert to its original shape once deformed. Furthermore, some applications, and particularly those "below the knee" (BTK) involve extremely narrow vessels or hard calcifications, for which balloon angioplasty may be contraindicated. Moreover, the application of pharmacological agents to a lesion for enhanced treatment may be desirable in some instances, and efficacy may be increased by actively scoring or slicing.

A desire also exists for active scoring of lesions, such as by making multiple passes. In this regard, others have proposed balloons for forming shallow cleavage lines or planes in the lesion or plaque (see, e.g., U.S. Pat. No. 8,323,243, the disclosure of which is incorporated herein by reference). Again, the use of a balloon is contraindicated for many applications, further increases the complexity, and does not readily allow for the cuts to be made in a variable manner, since the cutting depth depends on the inflation state of the balloon.

Accordingly, it would be desirable to provide a simple, yet effective slicing or scoring catheter for treating lesions that addresses the issue of elastic recoil by avoiding the need for an inflatable balloon. Such a catheter would be readily useful in a variety of hard-to-reach locations in the vasculature, including below the knee, where particularly hard calcifications might be present, and size constraints dictate a simpler and more effective approach than known proposals.

SUMMARY

An object of the invention is to provide a catheter with a retractable cutter for actively slicing/scoring a plaque, lesion (which may include part of a vessel wall), or other obstruction that addresses and overcomes the foregoing limitations, and possibly others that have yet to be discovered.

According to one aspect of the disclosure, a catheter for actively scoring or slicing a lesion is provided. The catheter includes a catheter body having first and second lateral openings. A cutter is connected to the catheter body, the cutter having a retracted configuration in which the cutter does not perform a slicing or scoring function and a deployed configuration for slicing or scoring the lesion. In the deployed configuration, a first blade projects from the first lateral opening and a second blade projects from the second lateral opening, and thus bilateral scoring or cutting may be achieved.

An actuator for actuating the cutter to move from retracted configuration to the deployed configuration may be provided. The actuator may comprise a manually operable wire extending to a proximal end of the catheter body. In some embodiments, the wire comprises a push-pull wire connected to the cutter, the push-pull wire having a first segment within a first lumen of the catheter body and a second segment within a second lumen of the catheter body.

In another embodiment, the wire is connected to a lever at a proximal end of the catheter body. The lever is adapted for pivoting to-and-fro in a circumferential direction to rotate the wire. At the distal end, the wire is connected to a pusher for causing the cutter (including opposed blades biased to a retracted position) to move to the deployed position. The pusher comprises a wedge for advancing the first and second blades radially to form the deployed configuration of the cutter. The wire may be connected to the pusher by a screw in order to translate rotational movement of the wire into linear movement of the screw and, hence, the pusher.

In still another embodiment, the cutter comprises a hub rotatably connected to the catheter body and associated with the actuator. The first and second blades are mounted to the hub for pivoting in moving the cutter from the retracted to the deployed configuration. The cutter further includes a third blade pivotally mounted to the hub, and a third lateral opening. The first, second, and third blades may each be circumferentially spaced approximately 120 degrees apart, and thus create a "trilateral" cutting or scoring catheter.

In any of the disclosed embodiments, a guidewire lumen is provided in the catheter body, as well as in the cutter, to allow for the catheter to track reliably to a desired treatment location or area in the vasculature. The lateral openings may also comprise elongated slits formed in an outer casing connected to a shaft to form the catheter body.

A further aspect of this disclosure pertains to a catheter for scoring or slicing a lesion. The catheter comprises a catheter body having first and second lateral openings, and a cutter body pivotally mounted within the catheter body. The cutter body has a retracted configuration in which it does not perform a slicing or scoring function, and a deployed configuration for slicing or scoring the lesion in which the cutter body projects both from the first lateral opening in a first direction from the second lateral opening in a second direction. An actuator, such as a push-pull wire, may be connected to the cutter body, the push-pull wire having a first segment within a first lumen of the catheter body and a second segment within a second lumen of the catheter body.

Yet another aspect of this disclosure pertains to a catheter for slicing or scoring a lesion. The catheter comprises a catheter body having first and second lateral openings. A cutter connected to the catheter body includes a retracted configuration in which it does not perform a slicing or scoring function and a deployed configuration for slicing or scoring the lesion. In the deployed configuration, a first blade of the cutter projects from the first lateral opening in a first direction and a second blade of the cutter projects from the second lateral opening in a second direction. A pusher is also provided with within the catheter body for actuating the cutter. In one embodiment, the pusher comprises a wedge associated with a screw connected to a wire accessible at a proximal end of the catheter body.

Still a further aspect of the disclosure pertains to a catheter for slicing or scoring a lesion. The catheter comprises a catheter body including first, second, and third lateral openings. A cutter connected to the catheter body is provided to move between a retracted configuration in which the cutter does not perform a slicing or scoring function and a deployed configuration for slicing or scoring the lesion. In the deployed configuration, a first blade of the cutter projects from the first lateral opening, a second blade of the cutter projects from the second lateral opening, and a third blade of the cutter projects from the third lateral opening.

In one embodiment, the cutter comprises a hub rotatably connected to the catheter body, and the blades are mounted to the hub for pivoting in moving the cutter from the retracted to the deployed configuration. The first, second, and third blades may be laterally flexible for bending or flexing during withdrawal through respective lateral openings when the cutter returns to the retracted configuration. The blades may also be circumferentially spaced approximately 120 degrees apart.

Still further, the disclosure pertains to a catheter for actively scoring or slicing a lesion. The catheter comprises a catheter body including a retractable cutter deployable in at least two directions for scoring or slicing the lesion. The at least two directions may be opposing directions, and the retractable cutter comprises a single body including a blade for projecting in the at least two directions. Alternatively, the retractable cutter comprises two blades, each projecting in one of the at least two directions. The retractable cutter may be deployable in at least three directions, and may comprise three blades, each projecting in one of the at least three directions.

This disclosure also pertains to a method of actively scoring or slicing a lesion in a vasculature. The method comprises extending a plurality of blades from within a catheter body to a deployed configuration, and slicing or scoring the lesion using the plurality of blades in the deployed configuration. The method may further include the step of advancing and retracting the catheter body in a longitudinal direction (with the anterograde movement possibly occurring with the blades retracted, and the catheter body then being pulled through the lesion anterograde with the blades deployed to cause the desired scoring or slicing in an active manner).

The deploying step may be achieved in a variety of ways. In one, the deploying step comprises rotating a single body including the plurality of blades within the catheter body using a remote actuator. The deploying step may comprise advancing a pusher for engaging the blades within the catheter body using a remote actuator. The deploying step may comprise rotating a hub within the catheter body using a remote actuator.

In one embodiment, the extending step comprises extending the plurality of blades a first amount prior to the scoring step. The method further comprises extending the plurality of blades a second amount. Once the blades are extended to the second amount (which may be greater or less than the first amount), the scoring step is repeated.

The extending step may comprise extending each of the plurality of blades from the catheter body a different amount. The extending may be completed without changing the diameter of the catheter body supporting the plurality of blades. In other words, the variability of the depth of the slice or score created is independent of any adjustment made to the diameter of the cutter casing. The method may further include the step of causing the plurality of blades to bend laterally during retraction into the catheter body.

BRIEF DESCRIPTION OF THE DRAWING FIGURES

The above and further advantages of the invention according to the disclosure may be better understood by referring to the following description in conjunction with the accompanying drawings in which.

Figure 1:
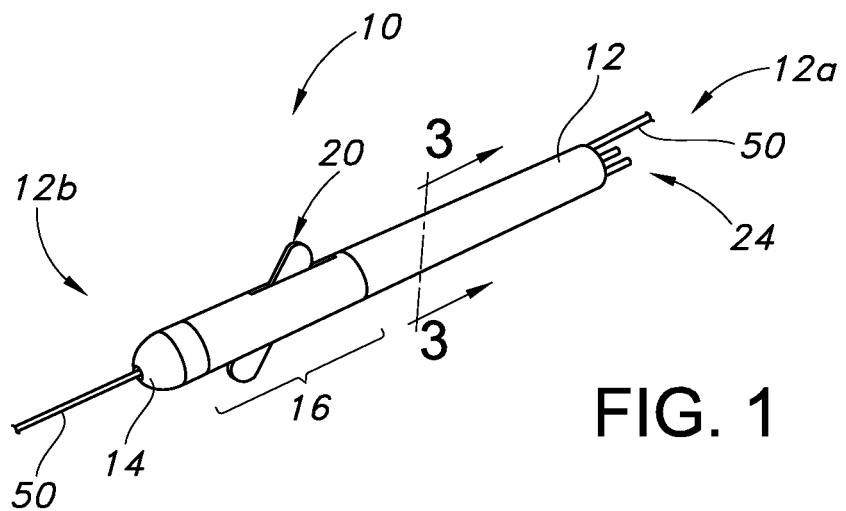
FIG. 1 is a perspective view of one embodiment of a slicing/scoring catheter according to the present disclosure.
Figure 2:
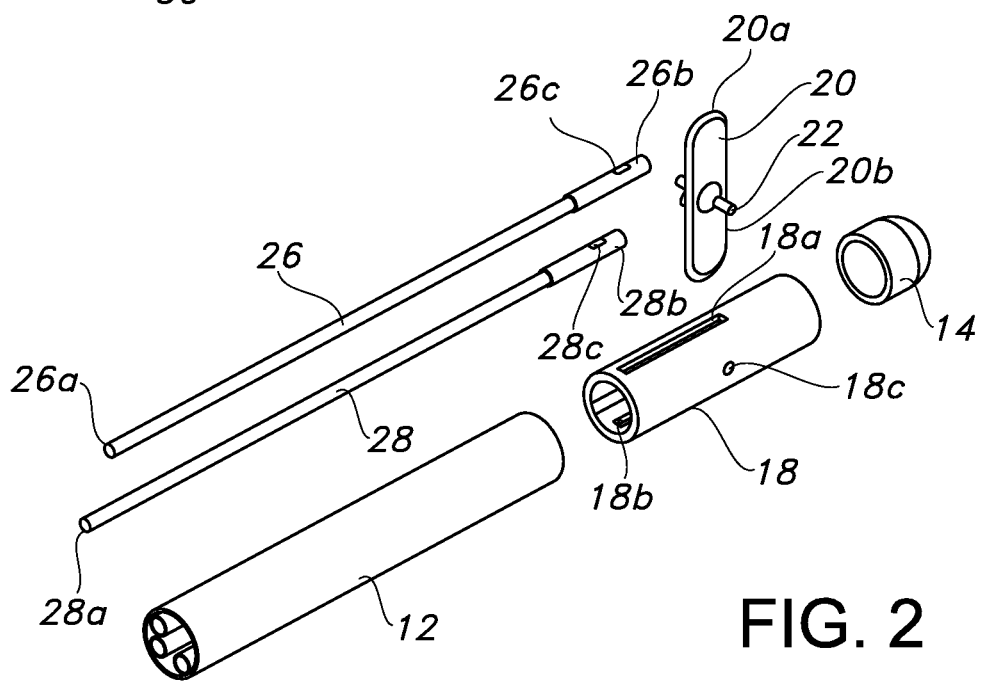
FIG. 2 is an exploded view of the catheter of FIG. 1.
Figure 3:
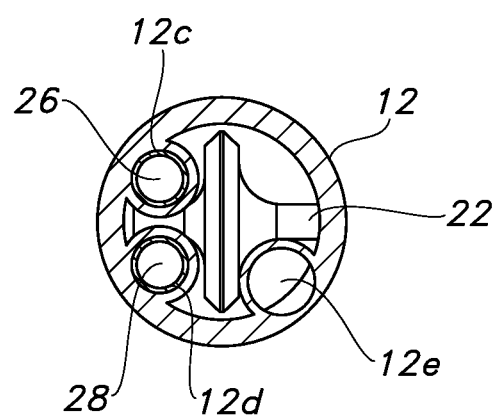
FIG. 3 is a cross-sectional view taken along line 3-3 of FIG. 1.
Figure 5:
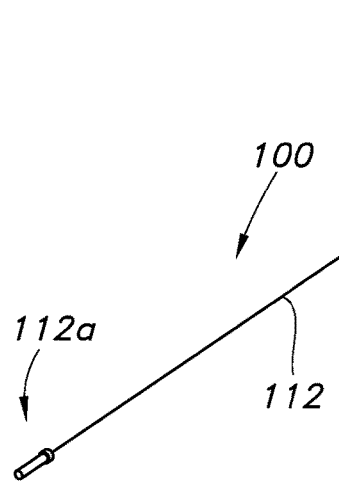
Figure 5A:
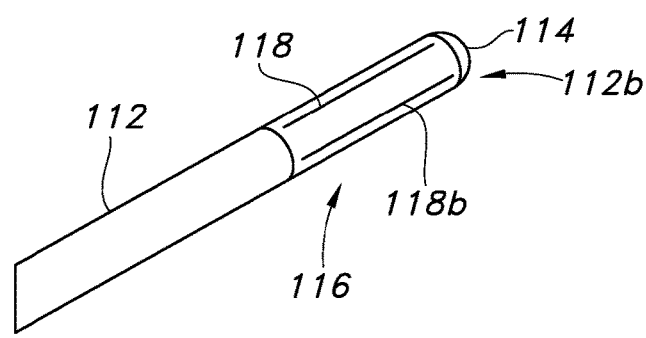
Figure 5B:
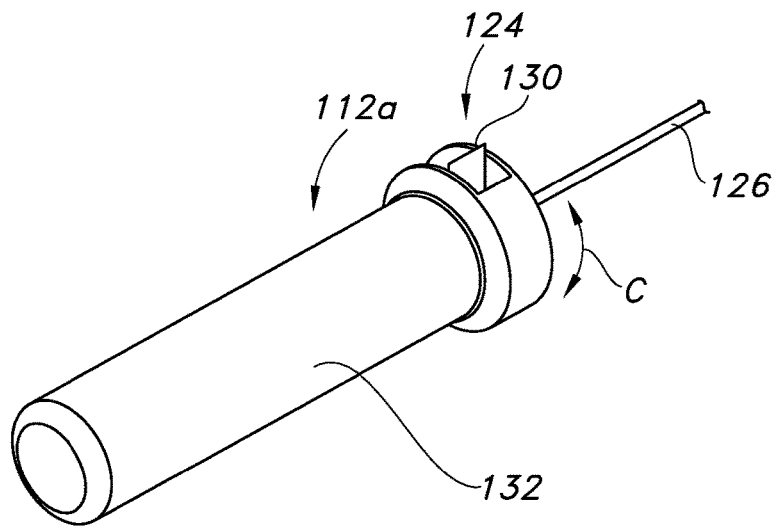
Figure 7C:
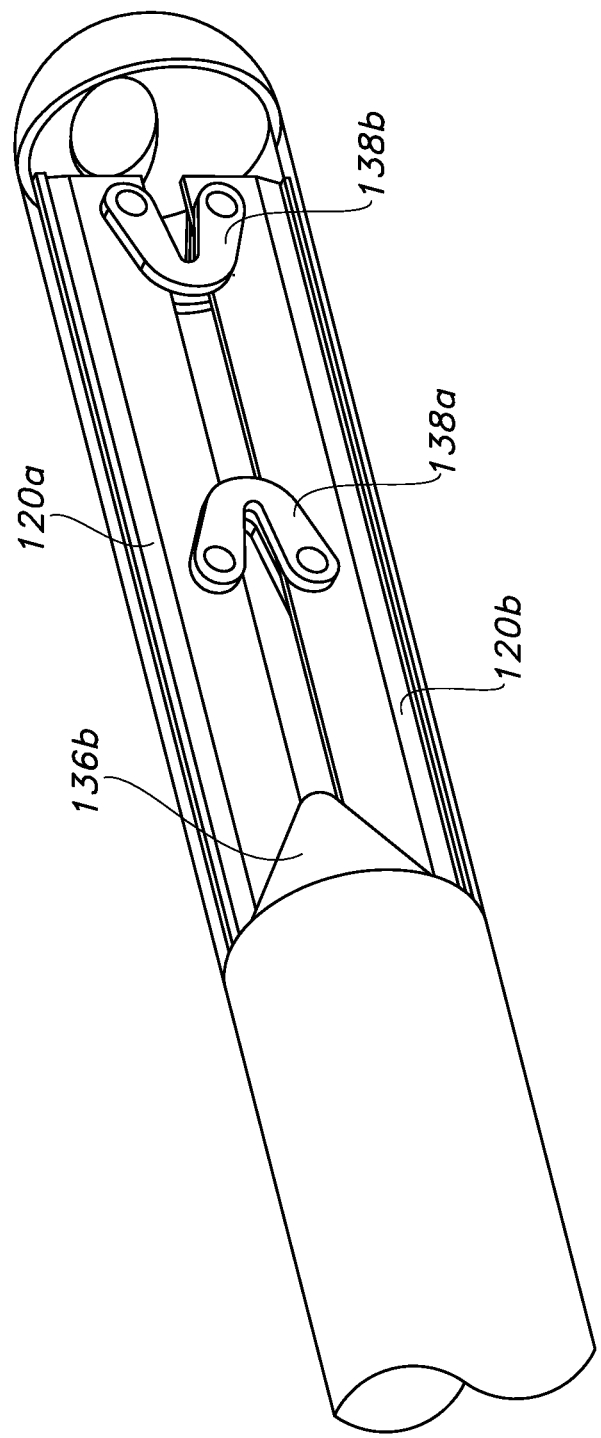
Figure 7D:
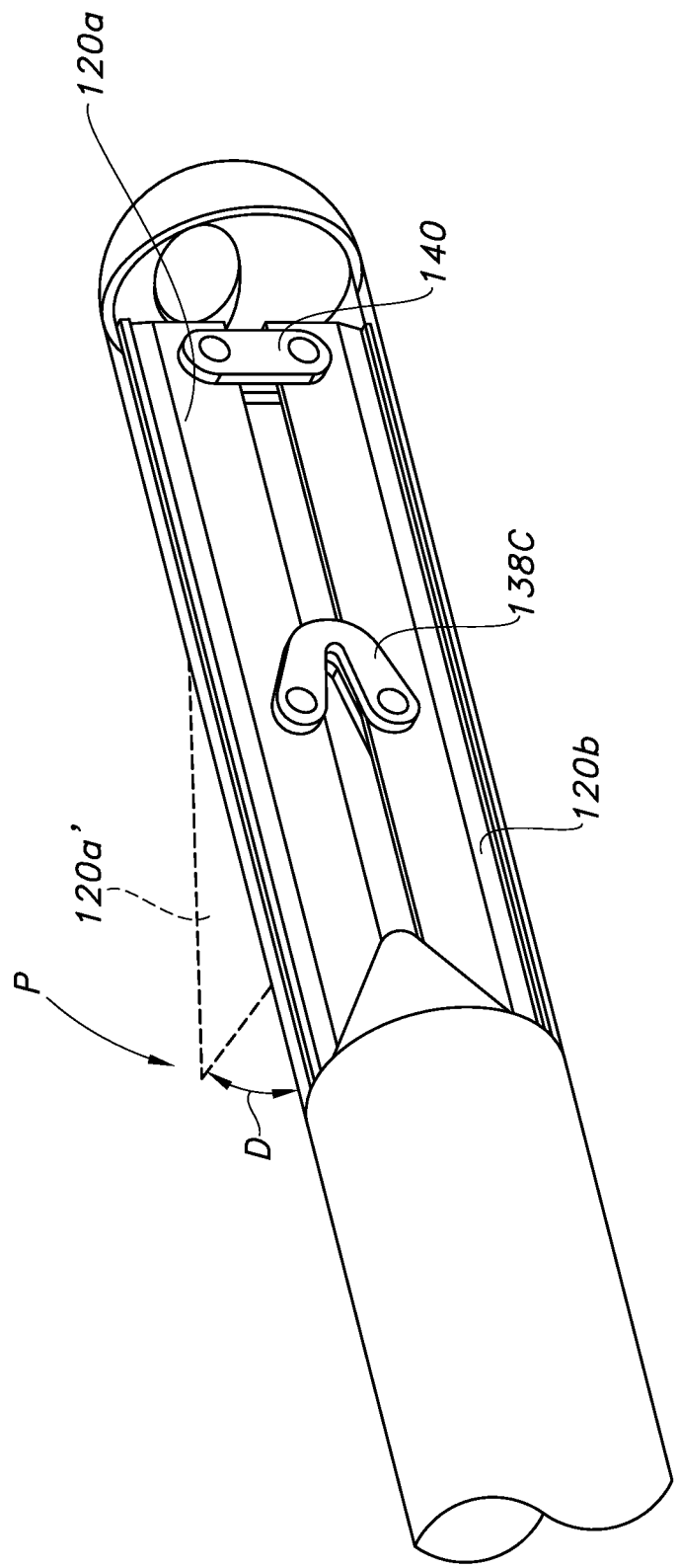
Figure 8:
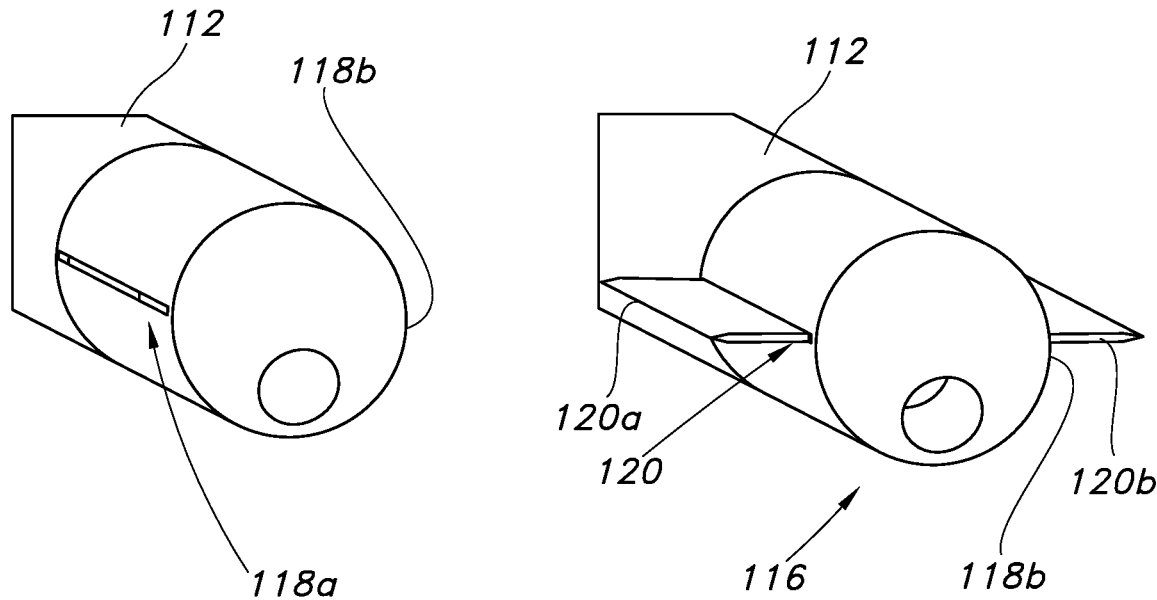
Figure 9:
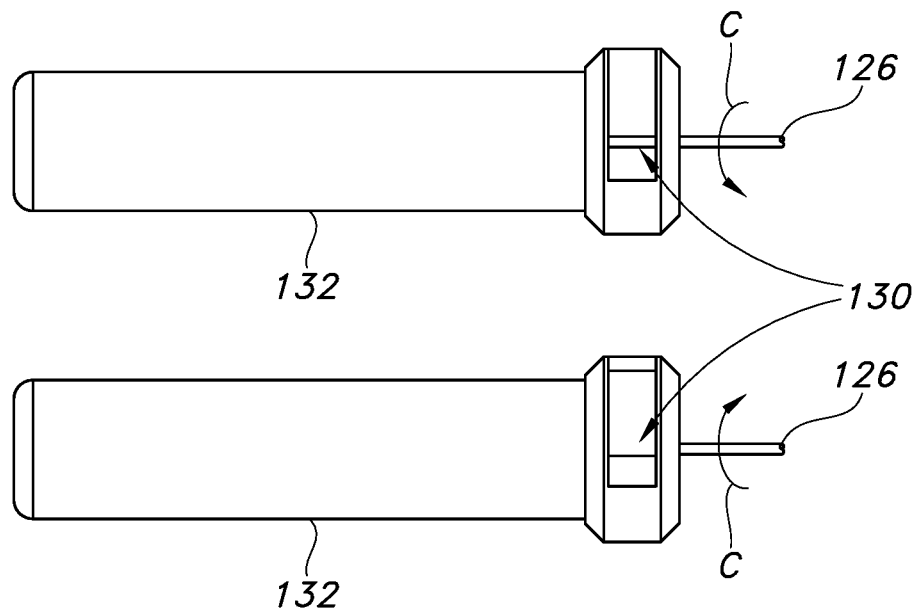
Figures 10, 11:
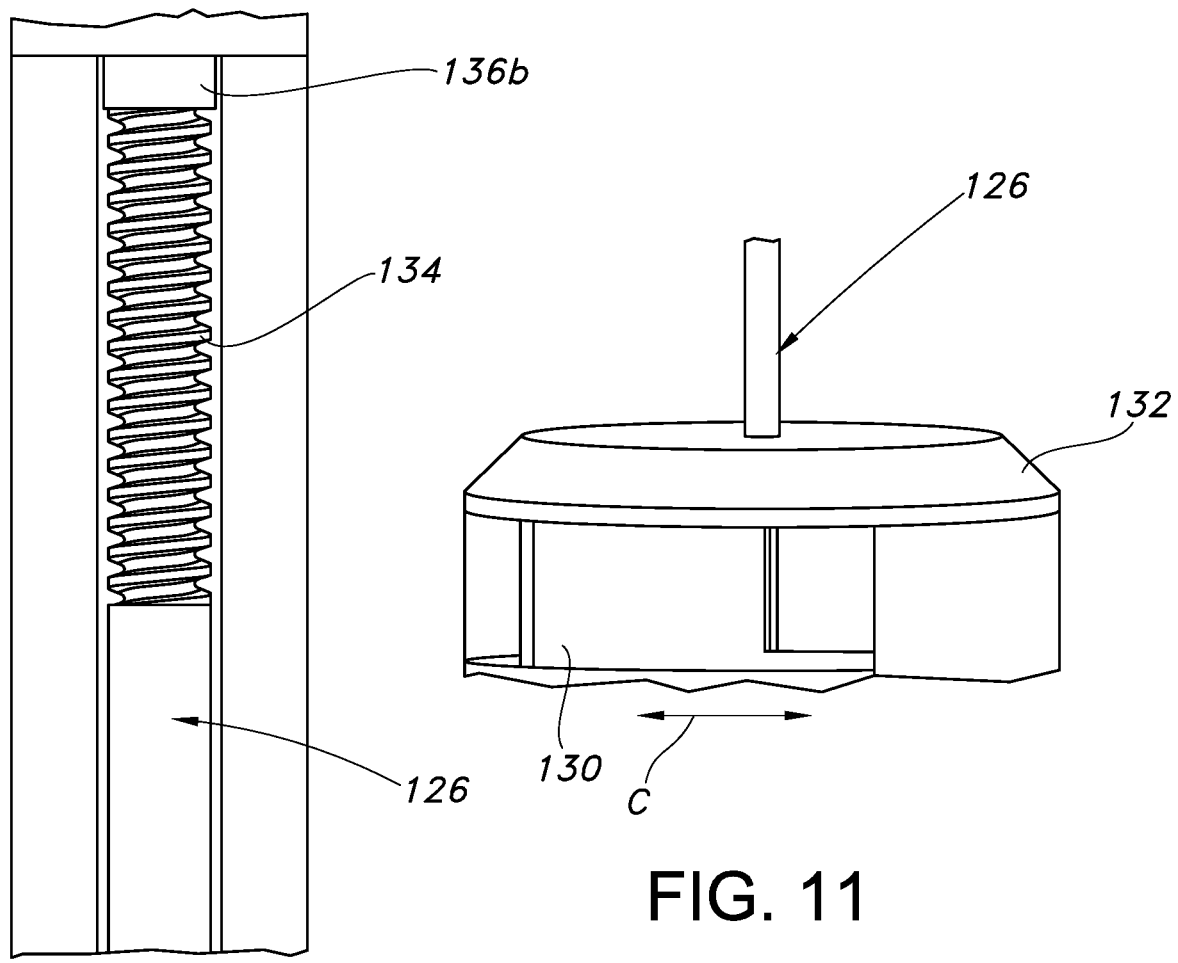
Figure 12:
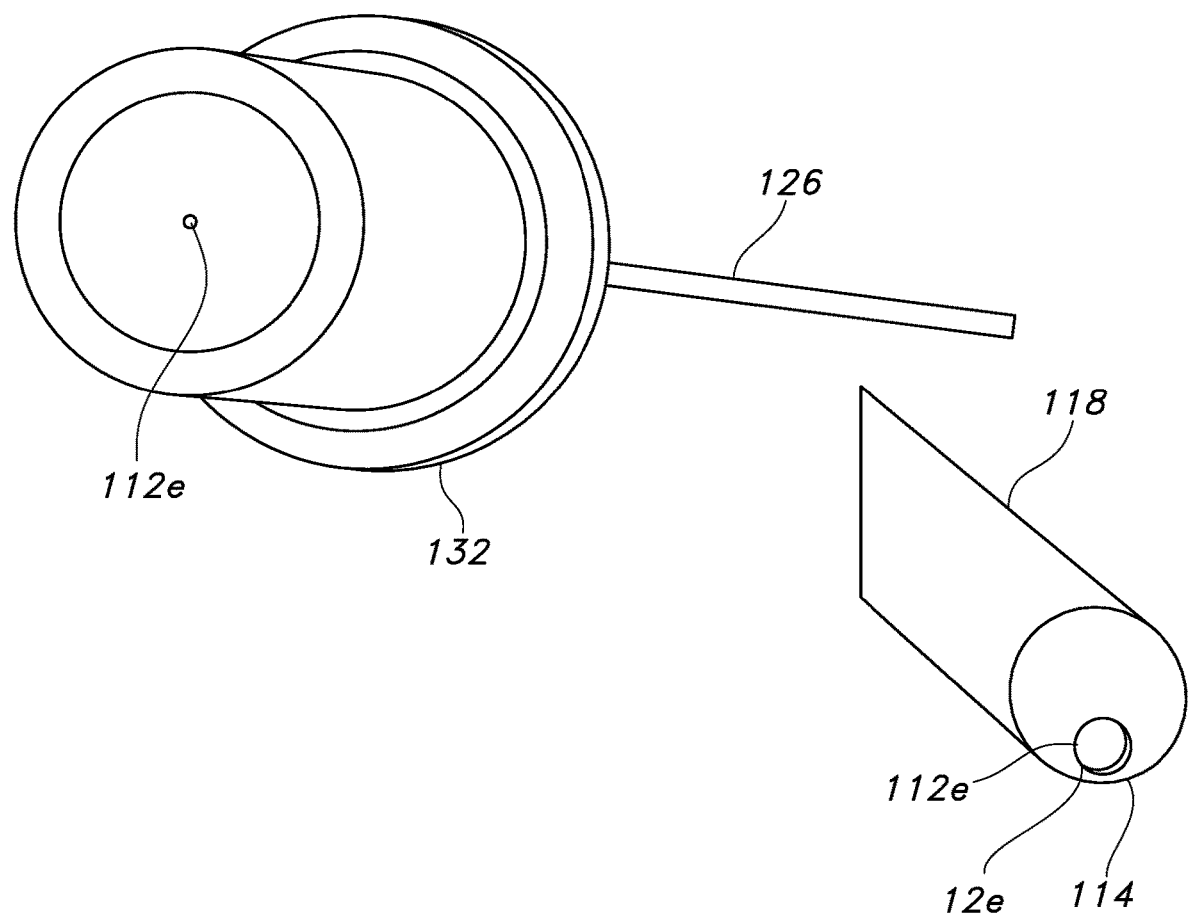
Figure 13:
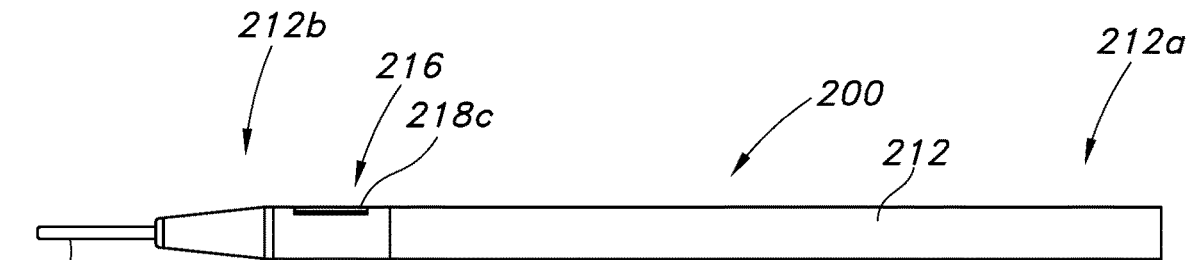
Figure 14:
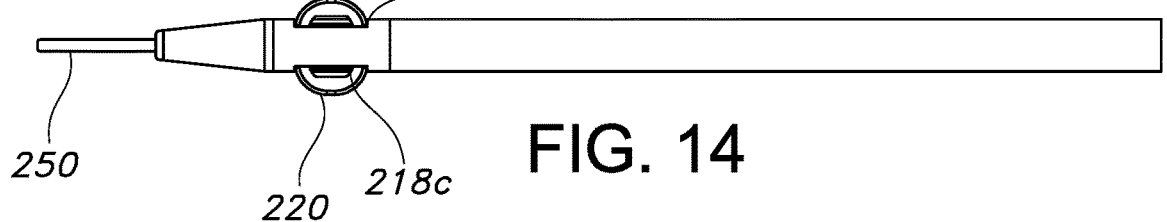
Figure 15:
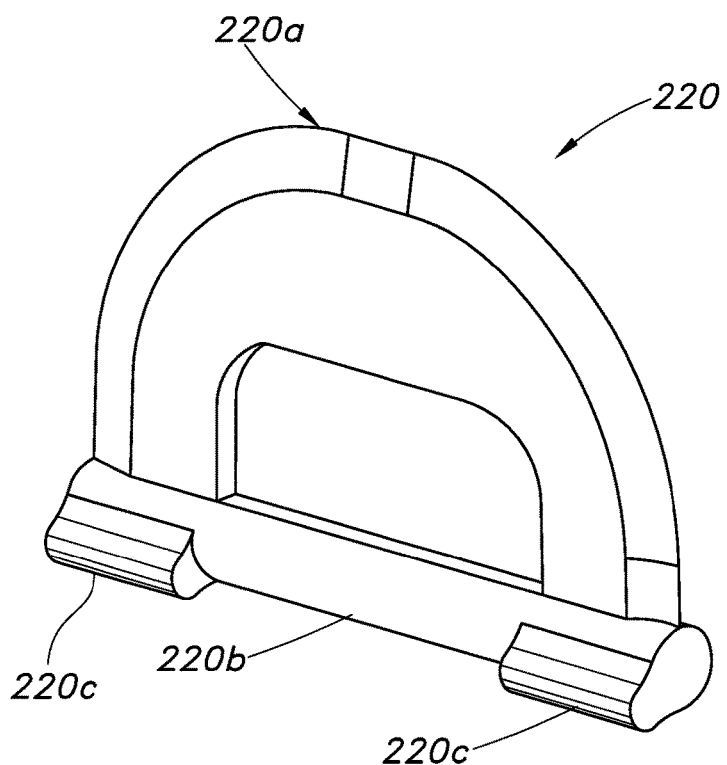
Figure 16:
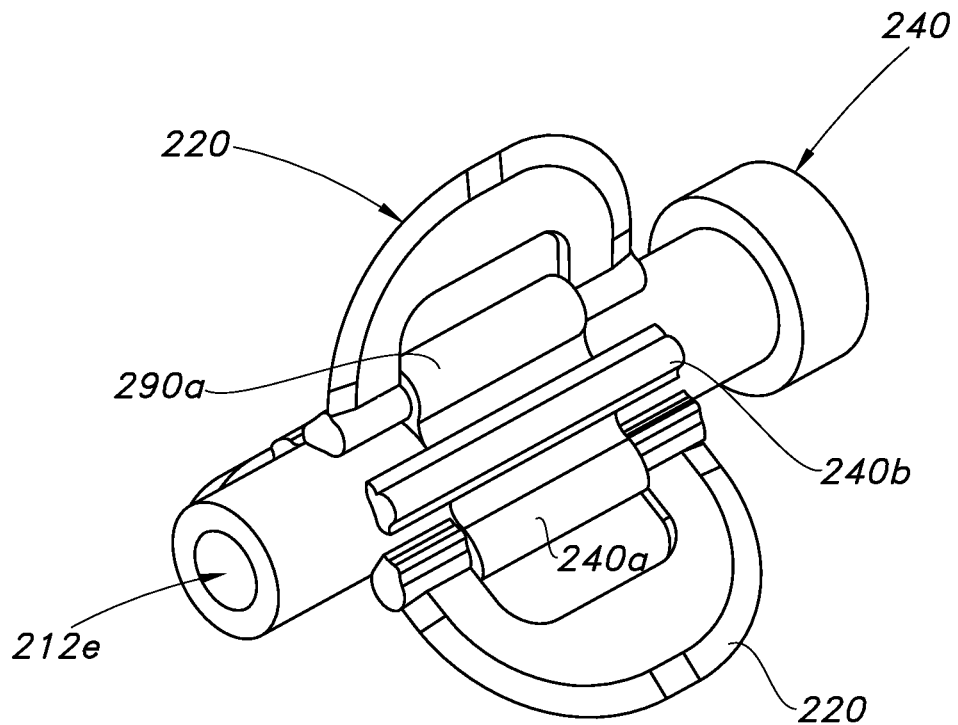
Figure 16A:
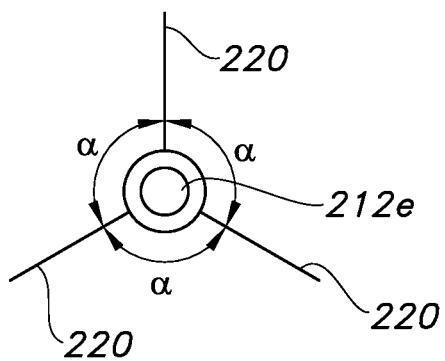
Figure 17:
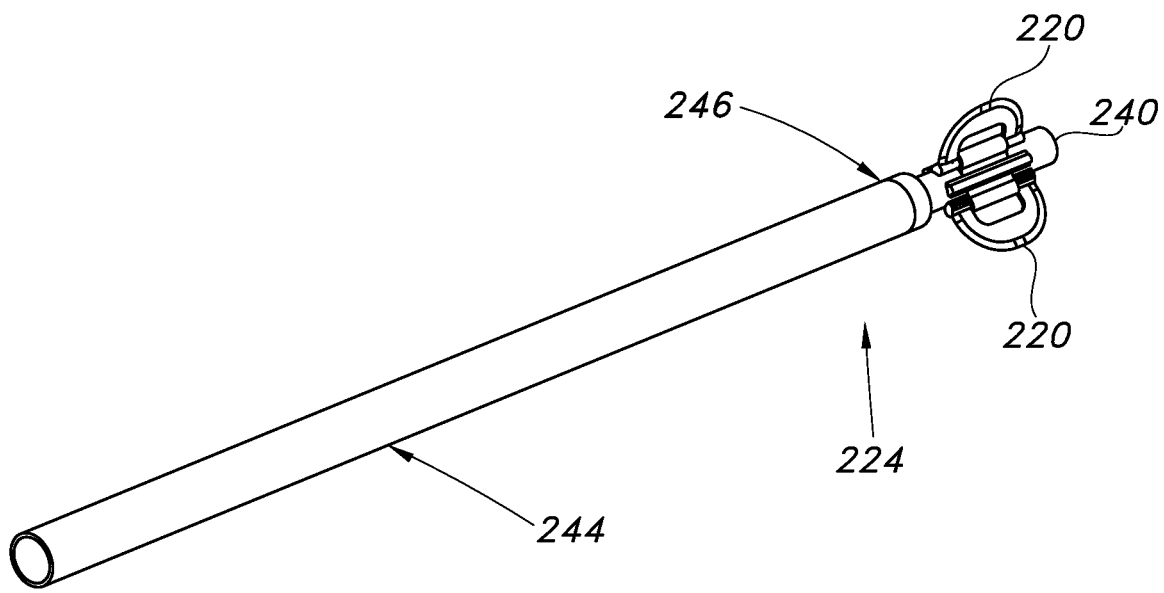
Figure 18:
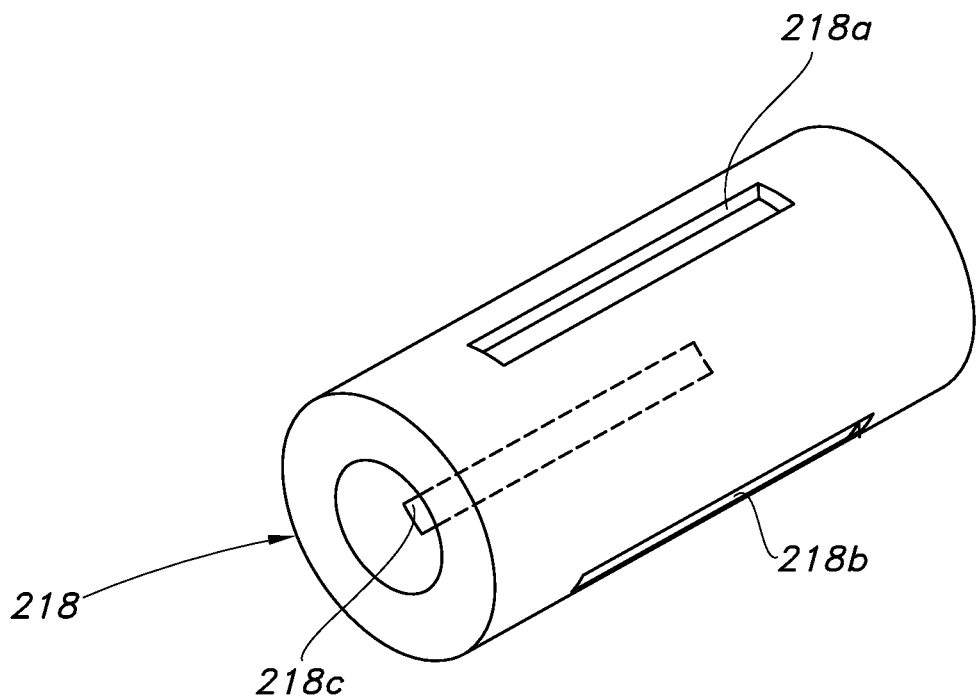
Figure 19:
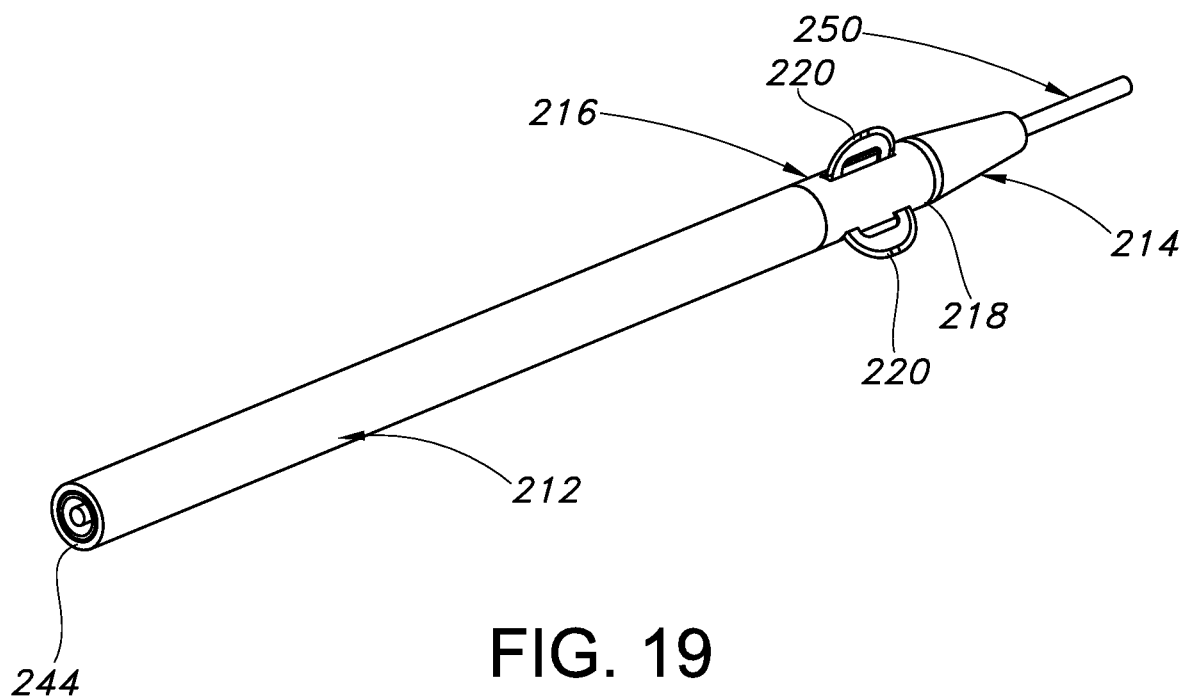
Figure 20:
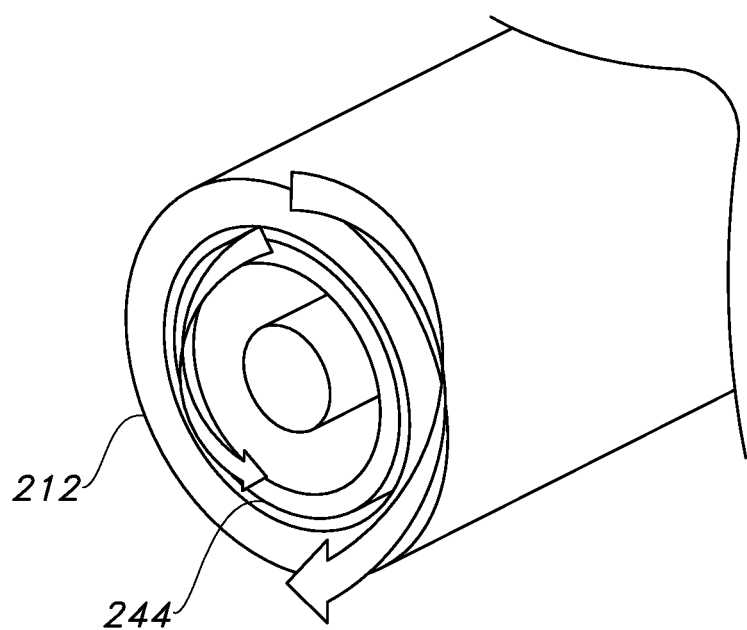
Figure 21:
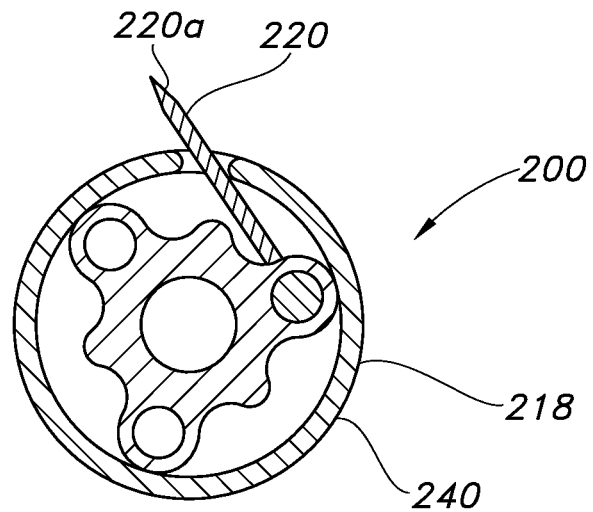
Figure 22:
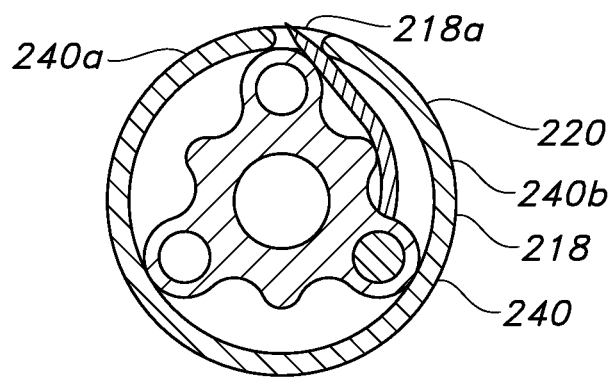

FIGS. 4, 4A, 4B, 4C, 4D, 4E, and 4F, and 4G are side and perspective cutaway views of the catheter of FIG. 1, and illustrate various operational states;

FIGS. 5, 5A, and 5B are perspective views of a second embodiment of a slicing/scoring catheter;

FIG. 6 presents a partially cutaway side view of a distal end of the slicing/scoring catheter of FIG. 5 in a retracted configuration, and FIG. 6A reflects the deployed configuration;

FIG. 7 presents partially cutaway, partially exploded side view of a distal end of the slicing/scoring catheter of FIG. 5 in a deployed configuration, and FIG. 7A reflects the deployed configuration;

FIGS. 7C and 7D are cutaway perspective views showing alternate arrangements for blade retention;

FIG. 8 presents cutaway perspective views of the catheter of FIG. 5 in the retracted and deployed configurations;

FIG. 9 presents cutaway side views of an actuator for the catheter of FIG. 5 in the retracted and deployed configurations;

FIG. 10 is a partially cutaway side view illustrating further detail of an actuator;

FIG. 11 is a partially cutaway side view illustrating further detail of an actuator;

FIG. 12 presents perspective views of the proximal and distal ends of the catheter of FIG. 5 to illustrate a guidewire lumen;

FIG. 13 is a side view of third embodiment of a slicing/scoring catheter in a retracted configuration;

FIG. 14 is a side view of the slicing/scoring catheter of FIG. 13 in a deployed configuration;

FIG. 15 is a perspective side view of a cutting portion or blade of the catheter of FIG. 13;

FIG. 16 is a perspective view of the cutter of the catheter of FIG. 13;

FIG. 16A is a schematic end view of the cutter of FIG. 16, illustrating the relative spacing of the blades of the cutter;

FIG. 17 is a perspective view of an internal portion of the catheter of FIG. 13, including the cutter;

FIG. 18 is a perspective view of a casing for receiving the cutter;

FIG. 19 is a perspective view of the catheter of FIG. 13;

FIG. 20 is a cutaway end view of the catheter of FIG. 13;

FIGS. 21 and 22 illustrate the bending of the blades when flexible during deployment and retraction.

The drawings are not necessarily drawn proportionally or to scale. For example, the dimensions of some of the elements may be exaggerated relative to other elements for clarity or several physical components may be included in one functional block or element. Further, sometimes reference numerals may be repeated among the drawings to indicate corresponding or analogous elements.

DETAILED DESCRIPTION

In the following detailed description, numerous specific details are set forth to provide a thorough understanding of the disclosed concepts. Those of ordinary skill in the art will know that the disclosed inventions may be practiced without these specific details. In other instances, well-known methods, procedures, components, or structures may not have been described in detail so as not to obscure the disclosed inventions.

The description provided below and in regard to the figures applies to all embodiments unless noted otherwise, and features common to each embodiment are similarly shown and numbered.

Referring first to FIGS. 1-4, a first embodiment of a slicing/scoring catheter 10 according to the disclosure is illustrated. The catheter includes an elongated body or shaft 12 having a proximal end 12a and a distal end 12b, which may include a tip 14. While elongated, the shaft 12 is illustrated in a compact form simply for ease of illustration, and would normally have a considerable length (e.g., 100-200 centimeters, or otherwise suitable to allow the distal end 12b to reach a treatment area of interest in the vasculature while the proximal end 12a remains accessible external to the vasculature).

Between the shaft ends 12a, 12b, a cutter 16 is provided for selectively providing a scoring/slicing function when deployed, but not providing such function when retracted or withdrawn. In the illustrated example, the cutter 16 comprises a casing 18 including a pair of elongated side openings, such as lateral slits 18a, 18b. A cutting portion of the cutter 16, such as a blade body 20, projects through these slits 18a, 18b when deployed (see partially deployed configuration in FIG. 1), such as for bilaterally scoring or slicing a lesion or otherwise providing a desired treatment in a living animal. Consequently, the blade body 20 may be thin in profile, having an elongated or oblong shape, with peripheral cutting edges or blades 20a, 20b provided along opposing surfaces thereof (such as the top and bottom edge, but the edge may also be continuous about the entire periphery of the blade body 20, as illustrated) for simultaneously slicing or scoring material. The opposite forward and rear ends of the blade body 20 may also be rounded to facilitate uninterrupted passage through the slits 18a, 18b when actuated and later returned to the retracted position.

In this example, the blade body 20 is mounted to the casing 18 for pivoting movement, such that the blades 20a, 20b thereof project through the slits 18a, 18b when actuated. The pivotable mounting may be achieved by providing the blade body 20 with a transverse axle 22, which may be unitarily formed with the body of the blade. The ends of the axle 22 may be rotatably retained within radially extending apertures 18c in the casing 18.

Figure 4:
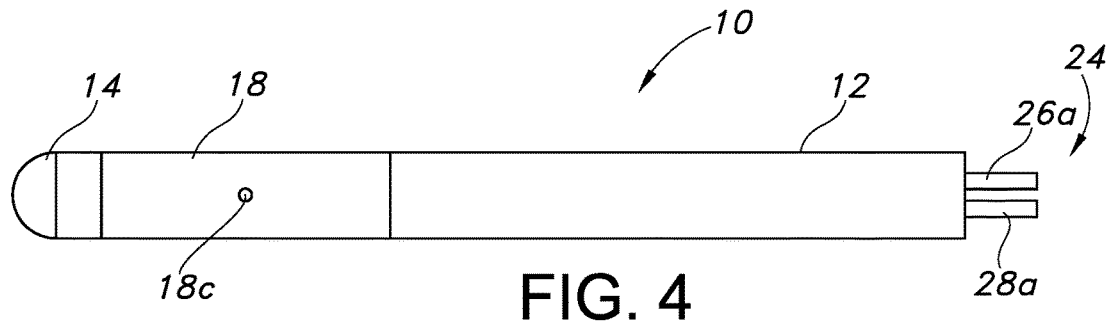
Figure 4A:
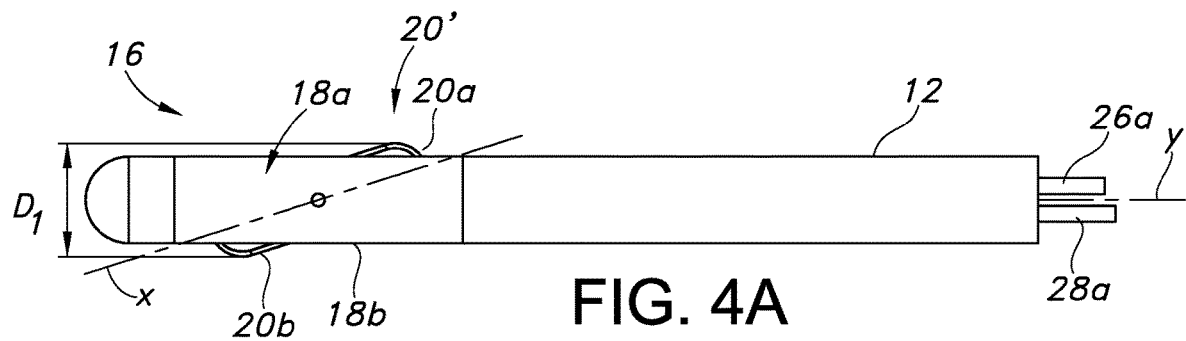
Figure 4B:
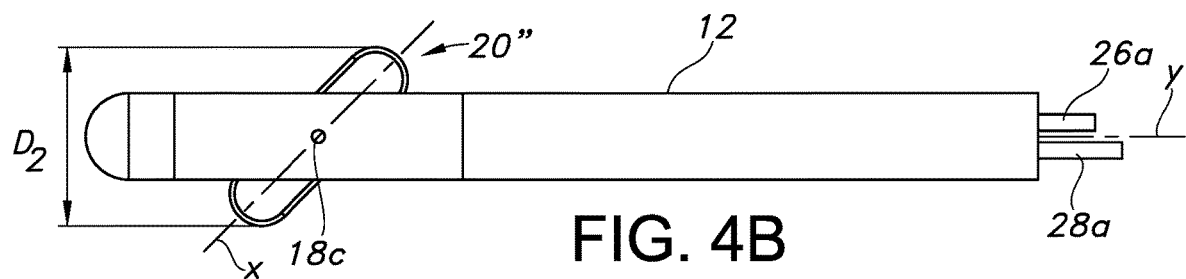
Figure 4C:
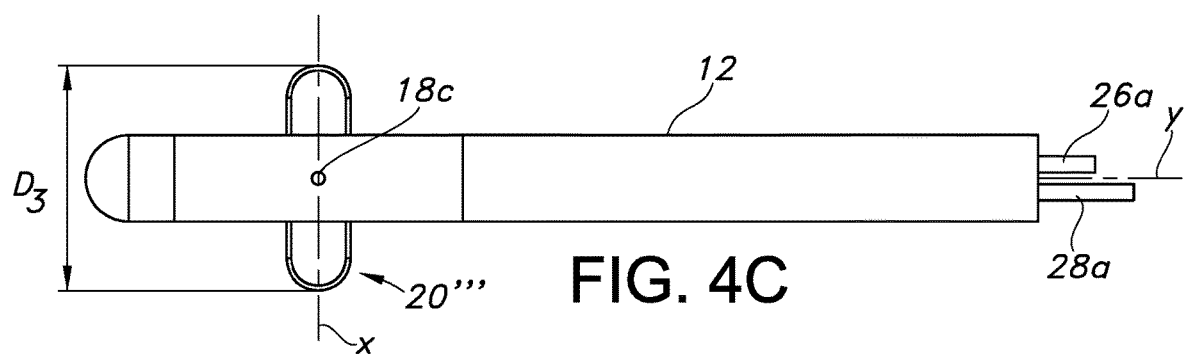
Figure 4D:
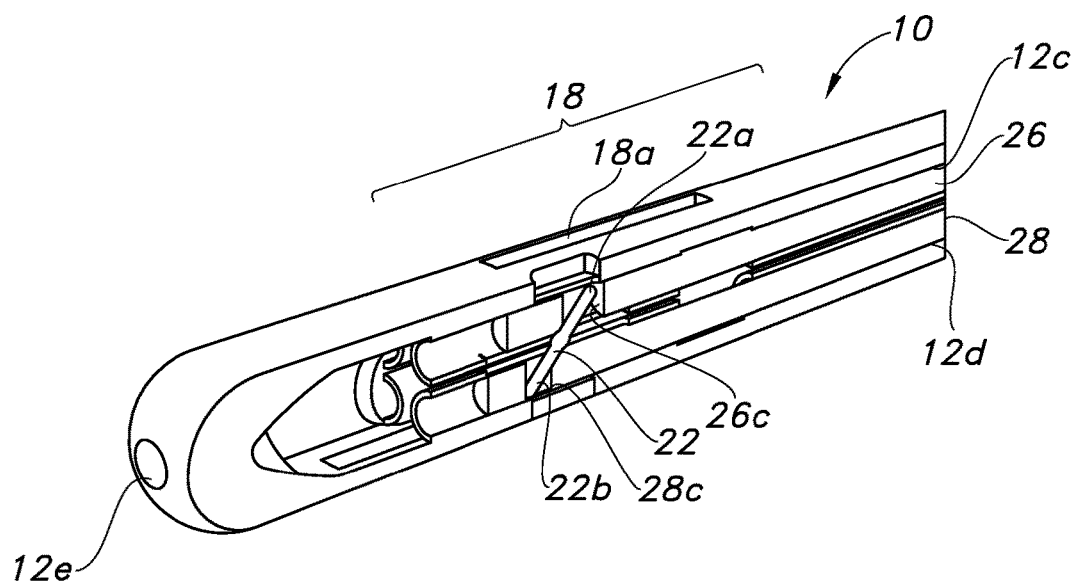

The catheter 10 further includes an actuator 24 for causing the selective actuation of the blade body 20. In the illustrated embodiment, the actuator 24 comprises a "push-pull" wire, which comprises of two individual and independently movable wire segments 26, 28, which as noted below may be connected. Specifically, each wire segment 26, 26 is located within a lumen 12c, 12d of the shaft 12 such that the proximal end portions 26a, 28a of the wire segments 26, 28 are accessible by a clinician at a proximal end 12a of the catheter 10 external to the vasculature. The distal ends 26b, 28b of the wire segments 26, 28 are connected to the blade body 20. This connection may be established by receivers in the form of transverse passages or slots 26c, 28c in the wires 26, 28 for receiving opposing cross-pins 22a, 22b projecting in opposite directions from an outer surface of the axle 22. These pins 22a, 22b may be oriented at an angle (e.g. 45 degrees) in the home position of the wire segments 26, 28, as best shown in FIG. 4D.

In use, the catheter 10 may be introduced to the vasculature via a guidewire 50 (see FIG. 1) received in a guidewire lumen 12e of the shaft 12, and extending though the cutter 16 and the tip 14. As can be appreciated from FIGS. 4 and 4D, the blade body 20 of the cutter 16 is fully retracted within the casing 18 in the non-deployed position, This provides the catheter 10 with the desired low profile (e.g., 4-5 French diameter) for tracking through the vasculature and, particularly, along small vessels below the knee (but of course other uses, such as above the knee use, are contemplated as well).

Figure 4E:
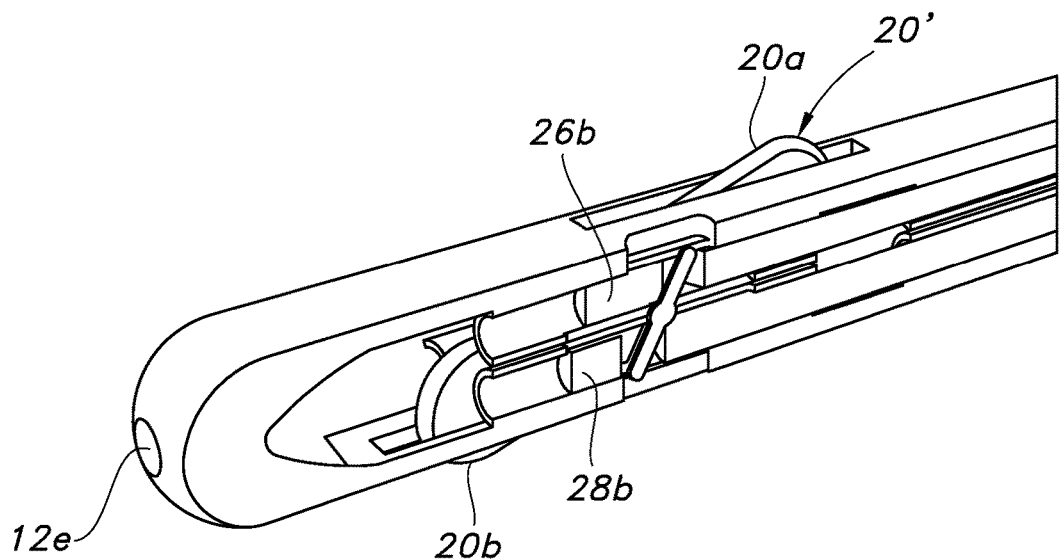

When scoring/slicing is desired, such as in proximity of a lesion or other obstruction (such as, for example, a clot), the cutter 16 may be at least partially deployed. This may be done remotely from the treatment area, such as outside of the vasculature/body, using the actuator 24, as indicated in FIGS. 4A and 4E. Specifically, pulling on the proximal end 28a of wire 28 and/or pushing on the proximal end 26a of wire 26 moves the distal ends 26b, 28b a corresponding amount (see FIG. 4E). This causes the blade body 20 (and, in particular, the blades 20a, 20b thereof) to at least partially alight from the casing 18 (see blade body 20') via the slits 18a, 18b for slicing or scoring (which may include moving the catheter 10 to-and-fro along the guidewire to create a longitudinal slice or score in the targeted material). The movement is such that ends of the blade body 20 extend in diametrically opposed directions (e.g., up and down in the illustration, but of course this could be any opposed directions within the vasculature).

As can be appreciated by comparing FIGS. 4A/4E, 4B/4F, and 4C/4G, the blade body 20 may be selectively actuated among a variety of pivoted positions, such as to rotate about the transverse axis of axle 22. In FIGS. 4A and 4E, the intermediate deployed position of blade body 20' is such that the cutter 16 has a first diameter D1 (e.g., 2 mm) that enlarges the catheter 10, and an axis of elongation X (or longitudinal axis) of the blade body 20 is at a small acute angle (e.g., 10-20 degrees) relative to an axis of elongation Y of the catheter 10.

Figure 4F:
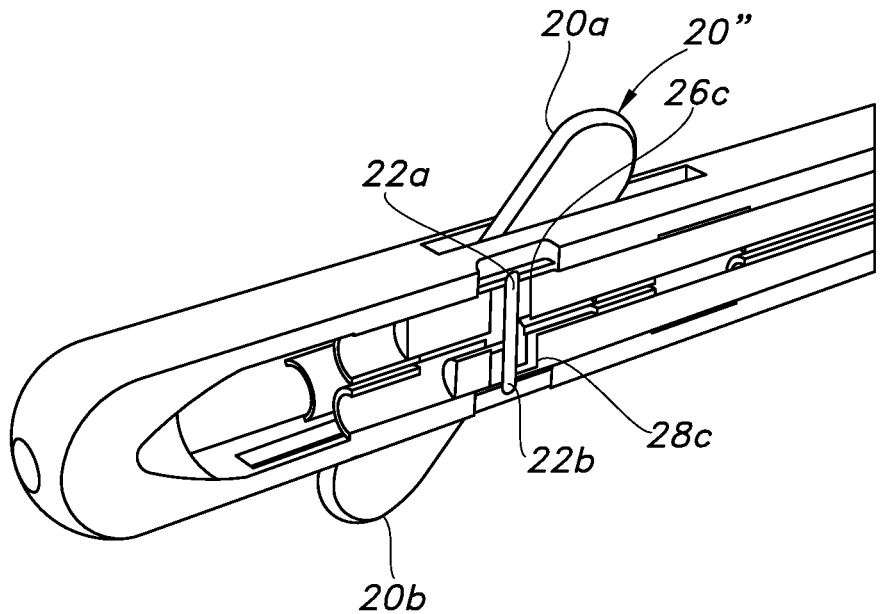

Continued actuation, such as by pulling on the proximal end 28a of wire 28, causes still further advancement of the blade body 20". This creates a diameter D2 (e.g., 3 mm) that is greater than diameter D1, and the relative angle of the axes X, Y is about 45 degrees, as shown in FIGS. 4B and 4F. Note that the cross-pins 22a, 22b are vertical (or orthogonal to the longitudinal axis of the wires 26, 28) in FIG. 4E.

Figure 4G:
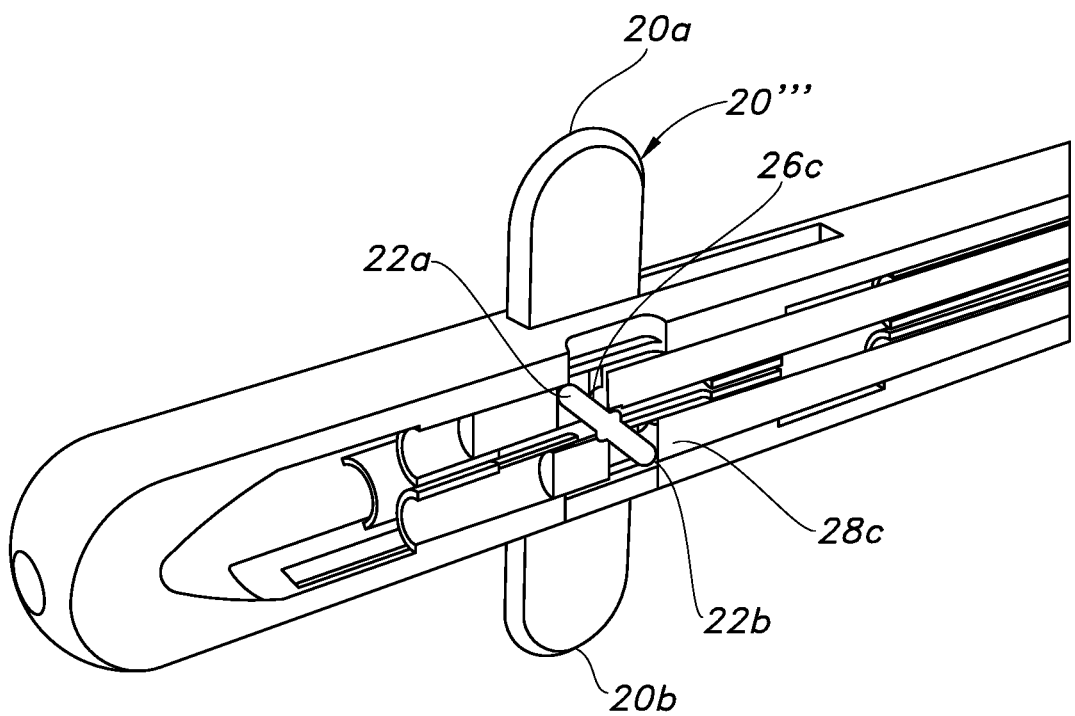

Still further actuation causes movement of the blade body 20''' to a still greater diameter D3 (e.g., 4 mm), which may reflect the maximum degree to which the wires 26, 28 may be pushed/pulled. The orientation may be such that the axis of elongation X of the blade body 20 is essentially perpendicular to the axis of elongation Y of the catheter 10, as shown in FIGS. 4C and 4G. Pins 22a, 22b are now fully reoriented as compared to FIG. 4D, with pin 22a projecting forwardly and pin 22b projecting rearwardly, but still remaining connected to wires 26, 28 by way of slots 26c, 28c.

It can be understood that actuation at any intermediate position between the fully deployed and fully retracted configuration of blade body 20 could also be achieved via simple manipulation of wires 26, 28 to other positions besides those shown. Moreover, such actuation could be actively controlled during advancement or retraction of the catheter 10 for purposes of creating different depths of scoring/cutting in an active manner or achieving other possible outcomes, without limitation.

As can be appreciated, pulling of wire 28 causes the actuation of blade body 20 in the above-described and illustrated manner. Consequently, as depicted, a distal end of the blade body 20 projects or alights from the rear end of slit 18a, and simultaneously the forward end of the blade body 20 alights and partially projects from the forward end of slit 18b. However, it can be readily understood that pushing wire 28 while pulling wire 26 causes the opposite positioning to occur. As can be appreciated, bodily rotating the catheter 10 about the longitudinal axis Y also changes the forward/rearward position of the blade body 20, and can also create a scoring effect in a circumferential direction.

Referring now to FIGS. 5-12, a second embodiment of a scoring/slicing catheter 100 is shown and described. The catheter 100 includes a tubular body or shaft 112 having a proximal end 112a and a distal end 112b. The distal end 112b includes a tip 114 and an adjacent cutter 116, which as shown in FIGS. 7 and 8 includes one or more selectively actuatable blades (two blades 120a, 120b shown), each of which has a supporting blade body 120. The blades 120a, 120b when retracted are located fully within a casing 118, and when actuated project from side or lateral openings, such as slits 118a, 118b, such as in first and second diametrically opposed directions (which is desirable, but considered optional, as the directions of the slits/blades could be orthogonal or otherwise not in direct 180 degree opposition).

As with the first embodiment, actuation of the blade(s) 120a, 120b may be achieved using a remote actuator 124. In a simple form, this actuator 124 again take the form of a "push pull" wire 126 (in the sense that it pushes and pulls another structure, albeit using a different type of mechanical connection, as outlined further in the following description). At the proximal end 112a of the catheter 100, the wire 126 may be connected to a lever 130 associated with a handle 132. The lever 130 may be mounted for moving to-and-fro in a circumferential direction C (see FIGS. 9 and 11), such as by thumb or finger action.

As can be understood by comparing FIGS. 6/6A and 7/7A, this relative movement of lever 130 causes the wire 126 to rotate as a result of the connection between these structures. This in turn causes a screw 134 within the shaft 112 to rotate relative to an internally threaded pusher 136 (including possibly by a substantial amount in the longitudinal direction, despite a relatively minor (¼ turn) movement of the lever 130, which may be achieved using a multiple (quad) lead screw, such that a minor turn of the wire 126 causes an amplified rotational movement of the pusher 136). Alternatively, a rotatable knob (not shown) associated with the handle 132 may be used to rotate the wire 126 multiple turns, and thereby rotate the screw 134. A slide associated with the handle 132 could also be used instead of rotational movement. In any case, this movement caused by the actuator 124 external to the vasculature advances the pusher 136 within the cutter 116 in the longitudinal direction to cause radial advancement of the blade(s) 120a, 120b, and allows for retraction when withdrawn.

As can also perhaps best be seen in FIGS. 6A and 7A, the pusher 136 comprises a housing 136a for receiving the screw 134 and a tapered distal end or wedge 136b for engaging tapered proximal inner portions of the blade(s) 120a, 120b during advancement. A spring 138 may be provided to bias the blades 120a, 120b toward the retracted or closed position, with the biasing force being sufficient to retain the blades when retracted, but overcome by the advancement of the pusher 136. Advancement to a position such that the pusher 136 is located between the blade(s) 120a, 120b not only overcomes the biasing force, but also prevents retraction (see left hand side image in FIG. 7), with the wedge 136b thus serving as a retainer for retaining the blades in the actuated condition and ensuring the desired slicing or scoring function may be reliably achieved without concern for inadvertent collapse. As indicated above, a single blade may be provided, and more than two may be provided, with each being associated with a single slit 118a, 118b and the pusher 136.

FIGS. 7C and 7D illustrate alternate arrangements for blade retention. In the FIG. 6 version, two springs 138a, 138b are provided to connect and bias the blades 120a, 120b. The springs 138a, 138b may be generally U-shaped and opposed. Together, the springs 138a, 138b provide a spring force that may be overcome by the linear advance of pusher (wedge 136b).

In the FIG. 7D version, a single spring 138c is provided, which may be at or near the midpoint of the blade lengths. Distally, a hinge 140 connects the blades 120a, 120b. Thus, actuation, such as via pusher (wedge 136b) causes the proximal end of the blades 120a, 120b to deploy (note action arrow D and partially deployed blade 120a'), but not the distal portion. As can be appreciated, this creates a raised point P that may be particularly useful for creating precision slices or scores in the vasculature (and control of the actuator 124 allows for the depth to be precisely controlled).

In use, the catheter 100 of this second embodiment may be advanced along a guidewire (not shown in FIGS. 5-12, but see, e.g., guidewire 50 in FIG. 1). This may be done via a lumen 112e in catheter 100 extending through shaft 112 from the proximal end of handle 132 to the distal end of the casing 118 via tip 114 (note lumens 112e) in parallel with the wire 126. Selective advancement of the blade(s) 120a, 120b between the fully retracted and fully actuated position, or any position therebetween, may be achieved using the actuator 124 (including lever 130). Return of the blades 120a, 120b is readily achieved using the actuator 124, such as by returning the lever 130 to an initial or home position, with the spring(s) 138 providing assistance.

A third embodiment of a scoring/slicing catheter 200 is shown in FIGS. 13-20. In this embodiment, the catheter 200 includes an elongated body or shaft 212, which has a proximal end 212a and a distal end. Adjacent the distal end 212b is a cutter 216, which is selectively actuated in a radial direction for scoring or slicing a lesion.

In the illustrated embodiment, and with reference to FIGS. 15, 16, and 16A, the cutter 216 comprises one or more blades 220, which may be generally C-shaped and pivotally mounted to an actuator 224 including a hub 240. Specifically, with reference to FIG. 15, it can be understood that three blade bodies 220 are present in this example, each of which includes a blade 220a along a radially distant portion thereof. A longitudinally extending support 220b is provided along a radially inward portion of each blade 220. The support 220b is rotatably mounted to the hub 240, such as in a journal 240a. A limiter or stop 220c may also be included for limiting the pivoting movement of each blade 220 in one direction.

As can be appreciated in FIGS. 16 and 16A, the blade bodies 220 when erected are radially oriented and circumferentially spaced. The spacing may be such that the blade bodies 220 are spaced at an angle α of 120 degrees. Thus, when three blade bodies 220 are present, as illustrated, the blades 220a are spaced equidistantly apart when actuated, and thus may provide "trilateral" scoring or slicing capabilities.

The cutter 216 further includes a casing 218, as shown in FIG. 18, which may be bonded (welded) or otherwise attached to form part of the shaft 212. The casing 218 includes side or lateral openings or slits 218a, 218b, 218c, each of which corresponds to one of the blade bodies 220 of the hub 240, which is located within the casing. The hub 240 in turn is connected to a tubular shaft 244, which is rotatable from a proximal end 212a of the shaft 212, and thus forms part of the actuator for the blade bodies 220. A tip 214 may be bonded to the distal end of the casing 218, as indicated in FIG. 19, and a guidewire lumen 212e may be provided through the tip 214, the hub 240, and the shaft 244 for receiving a guidewire 250.

Deployment of the blade bodies 220 to a cutting position from within the casing 218 involves actuating the actuator by rotating the shaft 244. This in turn rotates the hub 240 relative to the shaft 212 (see FIG. 20), and causes the blade bodies 220 to project through the respective slits 218a, 218b, 218c (compare FIGS. 13 and 14). When the actuator is held stationary, the limit or stop 220c holds the respective blade 220 in the erect, actuated position, and prevents over-rotation. The blade bodies 220 may have the same or different heights in the radial direction (which may also be done for blade bodies 20, 120), which may allow for the depth of the cut or slice made to be controlled through selective actuation or positioning of the catheter.

Scoring or slicing may then proceed in the desired manner and, when complete, reversing the actuator by counter-rotation of the shaft 244 causes the blade bodies 220 retract through openings/slits 218a, 218b, 218c, and the catheter 200 then has the normally low-profile configuration. To facilitate return of the blade bodies 220 to the housed/tucked/folded position, the material used may have some inherent flexibility, which thus allows the bodies to bend or flex and assume a slightly curved configuration when drawn into the casing 218. Yet, this flexibility does not compromise the scoring or slicing ability when deployed, especially since each blade body 220 when erected is bounded on either side by portions of the casing 216 in which the slits 218a, 218b, 218c are formed. As indicated in FIG. 16, a rest 240b may also be provided on the hub 240 to engage a corresponding surface of the blade body 220 when folded and thus oriented generally tangent to the hub 240.

The nature of folding of the blade body(ies) 220 when flexible is further illustrated with reference to the schematic views of FIGS. 21-22. FIG. 21 illustrates the hub 40 in a position where the blade tip or edge 220a is projecting from the casing 218, and thus partially actuated (and may have been drawn radially inward from a fully extended (perpendicular to the longitudinal axis) position. Continued rotation of the hub 240, as shown in FIG. 22, causes the lateral surface of the blade body 220 to engage the casing 218 adjacent to the slit 218a, and in light of the flexibility, assume a curved or bent configuration. The function of the rest 240b can be appreciated in terms of engaging a lateral side of the blade body 220, which may also engage the surface of the journal 240a adjacent to the tip 220a. The rotation may be limited such that the tip 220a is not fully withdrawn into the casing 218, and thus is able to readily extend upon rotation of the hub 218 using the remote actuator 224. Markers that are visible from outside of the body (e.g., radiopaque markers) may also be provided to allow for a clinician to readily assess the position or orientation of any part or portion of the catheter 10, 100, 200 (including on blade body(ies) 20, 120, 220, when in use).

The disclosure may also be considered to pertain to methods of treatment using the disclosed catheters 10, 100, 200, which may be done before, after, or in lieu of an angioplasty procedure. The method may involve advancing the selected catheter 10, 100, 200 along a guidewire 50, 250 to an area of interest or treatment area. Once positioned, the cutter 16, 116, 216 may be deployed, and the blade body(ies) 20, 120, 220 and associated blades 20a, 20b; 120a, 120b; 220a used for slicing, scoring, or cutting of an obstruction (e.g., a lesion), including by making multiple passes (and possibly at different depths by extending or retracting the blade body(ies) 20, 120, 220, or if the blade bodies have differing heights when actuated). The step may involve advancing the cutter 16, 116, 126 anterograde past the treatment area, deploying the blade body(ies) 20, 120, 220, then then pulling the catheter 10, 100, 200 retrograde along the guidewire 50, 150 to cause the scoring or slicing. When the desired scoring or slicing is completed, the blade body(ies) 20, 120, 220 may be retracted, and the above steps repeated (that is, the catheter 10, 100, 200 may be advanced past the lesion or treatment area, the cutters 16, 116, 216 deployed, and pulled through the lesion again). Once slicing or scoring is completed at a particular treatment location or area, the catheter 10, 100, 200 may be moved to another location for providing a treatment (such as scoring or slicing another lesion), or withdrawn from the vasculature.

In summary, numerous embodiments of a scoring/slicing catheter 10, 100, 200 are provided. Each embodiment relies on a simple remote actuator 24, 124, 224 to cause a cutter 16, 116, 216 to be actuated for scoring from a retracted position within an associated portion of a shaft 12, 112, 212, and thus allows for the catheter 10, 100, 200 to have the desirable low profile for purposes of tracking through the vasculature. The cutter 16, 116, 216 or, in particular, one or more blades 20a, 120a, 220a, may be selectively actuated to increase the radial extent of the catheter 10, 100, 200 to a desired degree for performing the desired scoring or slicing (such as after being advanced past the target treatment area), and then retracted for repeating the process or withdrawal. In all cases, the extension of the blade body(ies) 20, 120, 220 is completed without changing the diameter of the catheter body or shaft 12, 112, 212 for supporting the plurality of blades, which remains of a fixed diameter (unlike with an expandable balloon having surface cutting elements).

In any of the foregoing embodiments, the cutting blades 20, 120, 220 used may be provided with thin, razor edges of various shapes (flat, convex, chiseled, single bevel, double bevel, etc.) to provide a precision cut. The blade edges may also be serrated (single or double), scalloped, chamfered, wavy, or take other shapes or forms, depending on the particular use.

The disclosure may be considered to relate to the following items:

1. A catheter for actively scoring or slicing a lesion, comprising:
    a catheter body having first and second lateral openings; and
    a cutter connected to the catheter body, the cutter having a retracted configuration in which the cutter does not perform a slicing or scoring function and a deployed configuration for slicing or scoring the lesion using a first blade projecting from the first lateral opening and a second blade projecting from the second lateral opening.

2. The catheter of item 1, further including an actuator for actuating the cutter to move from retracted configuration to the deployed configuration.

3. The catheter of item 1 or 2, wherein the actuator comprises a wire extending to a proximal end of the catheter body.

4. The catheter of any of items 1-3, wherein the wire comprises a push-pull wire connected to the cutter, the push-pull wire having a first segment within a first lumen of the catheter body and a second segment within a second lumen of the catheter body.

5. The catheter of any of items 1-4, wherein the wire is connected to a lever at a proximal end of the catheter body, the lever adapted for pivoting to-and-fro in a circumferential direction to rotate the wire.

6. The catheter of any of items 1-5, wherein the wire is connected to a pusher for causing the cutter to move from the retracted to the deployed configuration.

7. The catheter of any of items 1-6, wherein the pusher comprises a wedge for advancing the first and second blades to form the deployed configuration of the cutter.

8. The catheter of any of items 1-7, wherein the wire is connected to the pusher by a screw.

9. The catheter of any of items 1-8, wherein the cutter comprises a hub rotatably connected to the catheter body and associated with the actuator, the first and second blades being mounted to the hub for pivoting in moving the cutter from the retracted to the deployed configuration.

10. The catheter of any of items 1-9, the cutter further including a third blade pivotally mounted to the hub.

11. The catheter of any of items 1-10, the cutter further including a third blade and a third lateral opening, the first, second, and third blades being circumferentially spaced approximately 120 degrees apart.

12. The catheter of any of items 1-11, further including a guidewire lumen in the catheter body.

13. The catheter of any of items 1-12, wherein the first and second lateral openings comprise elongated slits formed in an outer casing connected to a shaft to form the catheter body.

14. A catheter for actively scoring or slicing a lesion, comprising:
    a catheter body; and
    a cutter body pivotally mounted within the catheter body, said cutter body having a retracted configuration in which the cutter body does not perform a slicing or scoring function, and a deployed configuration for slicing or scoring the lesion by projecting the cutter body outwardly from the catheter body in opposing directions.

15. The catheter of item 14, further including a push-pull wire connected to the cutter body, the push-pull wire having a first segment within a first lumen of the catheter body and a second segment within a second lumen of the catheter body.

16. A catheter for actively slicing or scoring a lesion, comprising:
    a catheter body;
    a cutter connected to the catheter body, said cutter having a retracted configuration in which the cutter does not perform a slicing or scoring function, and a deployed configuration for slicing or scoring the lesion, and in which a first blade of the cutter projects in a first direction and a second blade of the cutter projects in a second direction; and a pusher within the catheter body for actuating the cutter.

17. The catheter of item 16, wherein the pusher comprises a wedge associated with a screw connected to a wire accessible at a proximal end of the catheter body.

18. A catheter for actively slicing or scoring a lesion, comprising:
    a catheter body including first, second, and third lateral openings; and
    a cutter connected to the catheter body, said cutter having a retracted configuration in which the cutter does not perform a slicing or scoring function, and a deployed configuration for slicing or scoring the lesion using a first blade projecting from the first lateral opening, a second blade projecting from the second lateral opening, and a third blade projecting from the third lateral opening.

19. The catheter of item 18, wherein the cutter comprises a hub rotatably connected to the catheter body, and the blades being mounted to the hub for pivoting in moving the cutter from the retracted to the deployed configuration.

20. The catheter of item 18 or item 19, wherein the first, second, and third blades are laterally flexible for bending during withdrawal through respective lateral openings when the cutter returns to the retracted configuration.

21. The catheter of item 18, 19, or 20, wherein the first, second, and third blades are circumferentially spaced approximately 120 degrees apart.

22. A catheter for actively slicing or scoring a lesion, comprising:
    a catheter body including first, second, and third lateral openings; and
    a cutter comprising a hub rotatably connected to the catheter body, the hub including at least one blade mounted for moving from a retracted configuration to a deployed configuration when the hub is rotated relative to the catheter body.

23. The catheter of item 22, wherein the cutter includes a casing for at least partially covering the hub, the casing including at least one lateral slit for receiving the at least one blade in the deployed configuration.

24. The catheter of item 22 or item 23, wherein the casing includes a plurality of lateral slits, and the hub includes a plurality of blades, each for projecting from one of the lateral slits in the deployed configuration.

25. The catheter of any of items 22-24, wherein the at least one blade is at least partially flexible for bending to pass through the at least one lateral slit when the hub is rotated.

26. A catheter for actively scoring or slicing a lesion, comprising:
    a catheter body including a retractable cutter deployable in at least two directions for scoring or slicing the lesion.

27. The catheter of item 26, wherein the at least two directions are opposing directions.

28. The catheter of item 26 or item 27, wherein the retractable cutter comprises a single blade for projecting in the at least two directions.

29. The catheter of any of items 26-28, wherein the retractable cutter comprises two blades, each projecting in one of the at least two directions.

30. The catheter of any of items 26-29, wherein the retractable cutter is deployable in at least three directions.

31. The catheter of any of items 26-30, wherein the retractable cutter comprises three blades, each projecting in one of the at least three directions.

32. A method of actively scoring or slicing a lesion in a vasculature, comprising:
    extending a plurality of blades from within a catheter body to a deployed configuration; and
    slicing or scoring the lesion using the plurality of blades in the deployed configuration.

33. The method of item 32, further including the step of advancing catheter body in a longitudinal direction with the plurality of blades in a retracted configuration past the lesion prior to the extending step, and wherein the scoring step comprises pulling the catheter body through the lesion with the blades in the deployed configuration.

34. The method of item 32 or item 33, wherein the deploying step comprises rotating a single body including the plurality of blades within the catheter body using a remote actuator.

35. The method of any of items 32-34, wherein the deploying step comprises advancing a pusher for engaging the blades within the catheter body using a remote actuator.

36. The method of any of items 32-35, wherein the deploying step comprises rotating a hub within the catheter body using a remote actuator.

37. The method of any of items 32-36, wherein the extending step comprises:
   extending the plurality of blades, a first amount prior to the scoring step; and
   extending the plurality of blades, a second amount; and repeating the scoring step.

38. The method of any of items 32-37, wherein the extending step comprises extending each of the plurality of blades from the catheter body a different amount.

39. The method of any of items 32-38, wherein the extending step is completed without changing the diameter of the catheter body for supporting the plurality of blades.

40. The method of any of items 32-39, further including the step of causing the plurality of blades to bend laterally during retraction into the catheter body.

41. The method of any of items 32-40, wherein the extending and scoring steps are completed after an angioplasty of the lesion.

Each of the following terms written in singular grammatical form: "a", "an", and "the", as used herein, means "at least one", or "one or more". Use of the phrase One or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or the context clearly dictates otherwise. For example, the phrases: "a unit", "a device", "an assembly", "a mechanism", "a component, "an element", and "a step or procedure", as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated components), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase "consisting essentially of." Each of the phrases "consisting of" and "consists of, as used herein, means "including and limited to". The phrase "consisting essentially of" means that the stated entity or item (system, system unit, system sub-unit device, assembly, sub-assembly, mechanism, structure, component element or, peripheral equipment utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional feature or characteristic" being a system unit system sub-unit device, assembly, sub-assembly, mechanism, structure, component or element or, peripheral equipment utility, accessory, or material, step or procedure, sub-step or sub-procedure), but only if each such additional feature or characteristic" does not materially alter the basic novel and inventive characteristics or special technical features, of the claimed item.

The term "method", as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Terms of approximation, such as the terms about, substantially, approximately, etc., as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

The invention claimed is:

1. A catheter for actively scoring or slicing a lesion, comprising:
   a catheter body having first and second lateral openings and a guidewire lumen;
   a cutter connected to the catheter body, the cutter including a blade body comprising a first blade and a second blade, the cutter having a retracted configuration in which the cutter does not perform a slicing or scoring function and a deployed configuration for slicing or scoring the lesion using the first blade projecting from the first lateral opening and the second blade projecting from the second lateral opening; and
   a push-pull wire connected to the cutter and adapted to move the cutter between the retracted configuration and the deployed configuration, the push-pull wire having a first segment within a first lumen of the catheter body and a second segment within a second lumen of the catheter body;
   wherein the blade body is a single blade body;
   wherein the blade body comprises a transverse axle; and
   wherein the first segment and the second segment of the push-pull wire each comprise a receiver, and wherein the transverse axle comprises a pair of projections for engaging the respective receivers.

2. The catheter of claim 1, wherein the first and second lateral openings comprise elongated slits formed in an outer casing connected to a shaft to form the catheter body.

3. The catheter of claim 1, wherein the catheter body comprises a casing, and wherein the transverse axle comprises ends which are rotatably retained within apertures in the casing.

4. The catheter of claim 1, wherein the first segment of the push-pull wire is adapted to push the blade body simultaneously with the second segment of the push-pull wire pulling on the blade body in order to transition the cutter between the retracted configuration and the deployed configuration.

\* \* \* \* \*